(12) United States Patent
Wintermantel et al.

(10) Patent No.: US 6,737,149 B1
(45) Date of Patent: May 18, 2004

(54) MEDICINAL PRODUCT WITH A TEXTILE COMPONENT

(75) Inventors: Erich Wintermantel, Niederrohrdorf (CH); Jörg Mayer, Niederlenz (CH); Erdal Karamuk, Zollikerberg (CH); Roland Seidl, Wattwil (CH); Bärbel Wagner, St. Gallen (CH); Bernhard Bischoff, Gossau (CH); Mario Billia, Münchwilen (CH)

(73) Assignee: Tissupor AG (CH)

( * ) Notice: Subject to any disclaimer, the term of this patent is extended or adjusted under 35 U.S.C. 154(b) by 0 days.

(21) Appl. No.: 09/890,635

(22) PCT Filed: Jan. 28, 2000

(86) PCT No.: PCT/CH00/00041

§ 371 (c)(1), (2), (4) Date: Oct. 29, 2001

(87) PCT Pub. No.: WO00/45761

PCT Pub. Date: Aug. 10, 2000

(30) Foreign Application Priority Data

Feb. 4, 1999 (EP) .............................................. 99810089

(51) Int. Cl.⁷ .............................. B32B 3/24; A61F 2/02
(52) U.S. Cl. ....................... 428/131; 428/156; 428/141; 602/42; 602/43; 602/44; 602/45; 602/47; 623/23.76; 623/23.74

(58) Field of Search ................................. 428/131, 156, 428/141; 602/42, 43, 44, 45, 47; 623/23.76, 23.74

(56) References Cited

U.S. PATENT DOCUMENTS

| | | | | | |
|---|---|---|---|---|---|
| 4,047,252 A | * | 9/1977 | Liebig et al. | ............... | 623/1.52 |
| 5,569,273 A | * | 10/1996 | Titone et al. | ............... | 606/151 |
| 5,990,378 A | * | 11/1999 | Ellis | ........................ | 623/11.11 |

FOREIGN PATENT DOCUMENTS

GB 2252528 A * 8/1992

* cited by examiner

*Primary Examiner*—William P. Watkins, III
(74) *Attorney, Agent, or Firm*—Webb Ziesenheim Logsdon Orkin & Hanson, P.C.

(57) ABSTRACT

The present invention relates to a medicinal product with a textile component such as a wound compress having a surface containing a multiplicity of openings arranged in at least two hole patterns. The diameter of one opening of one hole pattern deviates from the diameter of an opening of another hole pattern by about at least a factor of 5. Better wound healing is achieved by adapting the structural and mechanical characteristics of the medicinal product to the characteristics of the target tissue.

11 Claims, 2 Drawing Sheets

MEDICINAL PRODUCT WITH A TEXTILE COMPONENT

BACKGROUND OF THE INVENTION

1. Field of the Invention

The invention relates to a medical product with a textile component, for example a wound compress, having the features of a multiplicity of openings, with at least two patterns of holes with groups of openings, the diameter of one opening of one hole pattern deviating from the diameter of an opening of another hole pattern in each case by about at least a factor of 5 from one another.

2. Description of the Related Art

In the medical sector, a number of textile products are known which are intended to externally promote wound healing, for example. Known medical products such as wound compresses consist for example of woven fabric, which has the disadvantage that it has a hard surface which adapts poorly to the wound. For this reason, many wound compresses are made up of knitted fabrics which are soft per se. They also have some degree of moisture absorbency. The softness of knitted fabrics arises from the movement of the threads within the interfacing. These abovementioned wound products have the disadvantage that they harden because of exudates emerging from the wound and thus lose their functional ability.

Known compresses have semipermeable membranes of polyurethane which permit the passage and exchange of gases and fluids and have in particular nonadhesive materials on the surface facing the wound in order to prevent them from firmly sticking to the wound. This very type of compress is not able to specifically promote the angiogenesis which is achieved with the surface structure according to the invention. U.S. Pat. No. 5,465,735 describes such a multi-layer wound dressing with a dense nonwoven which is intended in particular to permit less sticking to the wound.

SUMMARY OF THE INVENTION

Further possible uses of medical products with a textile component are, for example, the treatment of abdominal wall defects in the groin area or for strengthening soft tissue in other places. A corresponding technique is described in U.S. Pat. No. 5,569,273 which describes a hexagonal net structure of polypropylene monofilament yarns. Large openings are constructed between adjacent vertical mesh rows, into which body tissue can grow into the implant because of the pore structure. However, this product does not promote angiogenesis.

EP 870 820 discloses a nonadhesive wound dressing which, across its active area, has depressions containing a pharmaceutical carrier substance. The depressions are intended only for receiving and delivering an active substance. The nonadhesion of the wound dressing is emphasized.

Finally, EP 931 012 describes a compress which is used for treating wounds in a moist environment and which, by means of an appropriate choice of dressing material, is likewise intended not to adhere to the wound.

Taking this prior art as a basis, it is an object of the invention to make available a medical product which is of the type set out in the introduction and which specifically influences and promotes angiogenesis and the healing process associated with the latter.

It is also an aim of the invention to ensure that such a medical product also remains soft in its textile component even after prolonged contact with the wound.

A further aim of the invention is to ensure that the rigidness of such a medical product can be preset individually at the time of production.

Finally, it is also a further object of the invention to improve angiogenesis and consequently the tissue regeneration in leg ulcers, for example.

According to the invention, this object is achieved by the fact that the surface has a multiplicity of openings, there being at least two patterns of holes with groups of openings, the diameter of one opening of one hole pattern deviating from the diameter of an opening of another hole pattern in each case by about at least a factor of 5 from one another.

The advantage for the patient of using medical products according to the invention lies in the more rapid wound healing, in the reduction of the pain associated with wound treatment, in the shorter time spent in an inpatient department, and in the fact that the cost of treating such wounds is considerably reduced, which is important to the economy. These advantages are achieved by adapting the structural and mechanical properties of the medical product to the properties of the tissue in question.

In the case of leg ulcers, the main focus of wound healing lies in the regeneration of a physiologically functional vascular system. Wound healing is to be seen in the context of scar tissue formation. An intensive scar tissue formation inconveniences the patient because of the poor cosmetic aspect and in particular because of limited mobility. Both of these lead to personal anxiety and in many cases to disability. When the wound has healed, there is unfortunately connective scar tissue left in which the collagen matrix is reconstructed in compact parallel bundles, whereas the meshwork in undamaged skin has mechanically better properties.

Rapid vascularization can lead to uncontrolled formation of the skin capillary system. The capillaries themselves influence the orientation of the collagen fibers.

Mechanical signals in the form of the exertion of a controlled pull on the cells in the wound bed can represent an important activator of the wound response. Mechanical influences on the wound also play a part in collagen genesis because modified stresses during wound closure influence scarring. It is assumed that in order to form a normal collagen architecture a defined physiological mechanical stimulation is required with respect to loading and orientation. In the case of scar tissue, by contrast, the anisotropy of the collagen network and the dimensions of the collagen fibers are increased.

In contrast to the feature of nonadhesion to the wound bed, on which feature emphasis is placed in the prior art, growth of tissue into the medical article is here desired and advantageous.

The invention makes available a wound treatment system developed on a textile basis which controls tissue formation and positively influences angiogenesis by acting as a framework. The support for the layer according to the invention is dependent on the application. The use of the medical products according to the invention is possible in many areas. One area of use concerns the treatment of large wounds, burns or in surgical applications, for example for hernia meshes. These procedures require treatment systems which make it possible to minimize scar formation. At the same time, it is also possible for the medical products to include mannose-6-phosphate or other collagen-regulating means, or factors which promote tissue regeneration, for example growth factors of the TGF-b family.

The medical product can be used in many applications where the embroidery-specific properties such as the controlled mechanical properties of an embroidery, the local variation in the mechanical design and the specific porosity can be of great advantage. In addition to the stated compresses and hernia meshes, these include abdominal wall replacements, artificial blood vessels and artificial ligaments. In the case of the latter, the embroidery technique can be used to pass from a first specific structure, where the ligament is to grow on and where load transmission takes place, to a second and different structure in the ligament area. A further application is the formation of augmentation embroideries for reconstruction of the jaw bone in the dental sector.

Depending on the desired mechanical and structural properties of the textile, different yarn types are used. These can include fibrous, multifilament or monofilament yarns, which can also be untreated, antimicrobially pretreated, gel-coated and can be present in different titers.

By using embroidery technology, the knot size and the nature of the linking can likewise be preset.

The invention is described in more detail below on the basis of illustrative embodiments.

BRIEF DESCRIPTION OF THE DRAWINGS

FIG. 1 shows a medical article 1 according to the invention in a diagrammatic cross section. This medical article is made up of three layers, for example. A base layer remote from the wound consists of compact woven fabric 10 which has an antibacterial action. This also controls the oxygen and water content at the same time.

DETAILED DESCRIPTION OF THE PREFERRED EMBODIMENTS

Figure 1:
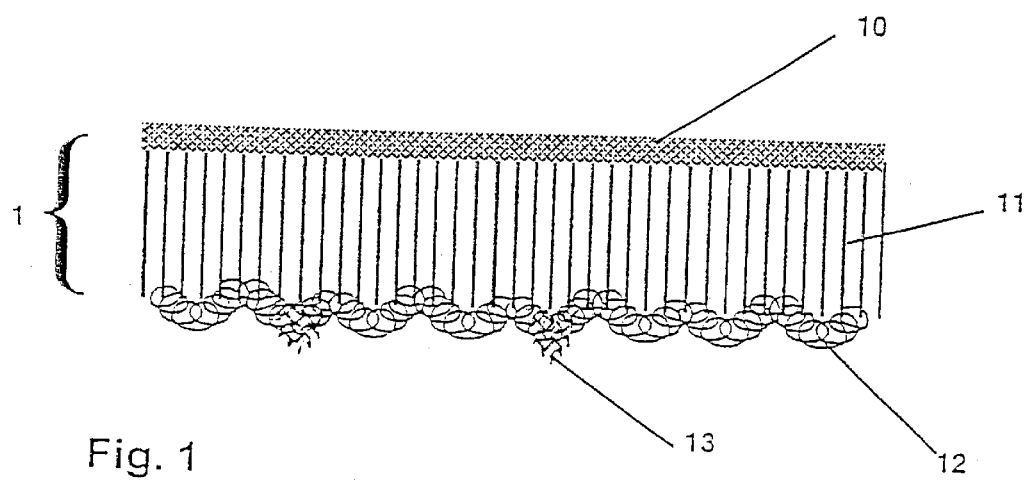
FIG. 1 is a diagrammatic cross section through a medical article according to one illustrative embodiment of the invention.

A spacer layer 11 with high shear force takeup consisting of gel-modified yarns permits absorption and desorption and the mechanical binding of the compress material. The shear force takeup permits the distribution of local pressure loads, that is to say it has a cushion function and permits stress distribution, which leads to uniform loading of the wound surface and thus avoids negative local stresses. Lastly, the compress 1 has an embroidered layer 12. The fabric 11 is designed as a spacer in relation to the antibacterial layer 10 and as a material which takes up exudate. On this fabric 11, which is advantageously formed as a knit, lies the separately produced embroidered layer 12 which is preferably connected at its side edges to the compress 1, for example by ultrasonic welding. Reference number 13 denotes stimulation points which are formed in the layer 12, particularly in the embroidery technique. In the form represented, they form flat to semi-round protuberances, stimulation points 13, facing toward the wound surface and they can also protrude from the side facing away from the wound surface. The stimulation points 13 can all be the same size or can differ in size individually or in groups. The word "size" in this case refers both to the height above and below the surface of the embroidery and also to the surface area in the plan view of the figures. Gradients in size can be provided, for example with the stimulation points 13 with the largest surface area and the smallest thickness in the middle of an embroidery, and the stimulation points 13 with the smallest surface area and the greatest thickness at the edges of the embroidery. Any other combination of thicknesses and surface areas can be used.

An embroidered structure 12 and thus an angiopolar layer is thus provided near the wound. An angiopolar layer is a layer which permits the specific oriented growth of blood vessels into a structure and thus influences the density and orientation of the blood vessels in the regenerated tissue. This embroidered structure 12 introduces morphological features into wound treatment which induce and stimulate a specific angiogenesis within the framework and thus form the physiological basis for tissue renewal.

The textile architecture 11 and 12 creates optimum mechanical support, forms a reservoir for exudates and permits optimum control of moisture and gas transport.

With the embroidery technique, highly architectured three-dimensional textile structures are obtained which are needed for structural functions, for example pore pattern, for angiogenesis. The embroidery technique permits any desired use of materials in base fabrics.

Figure 2:
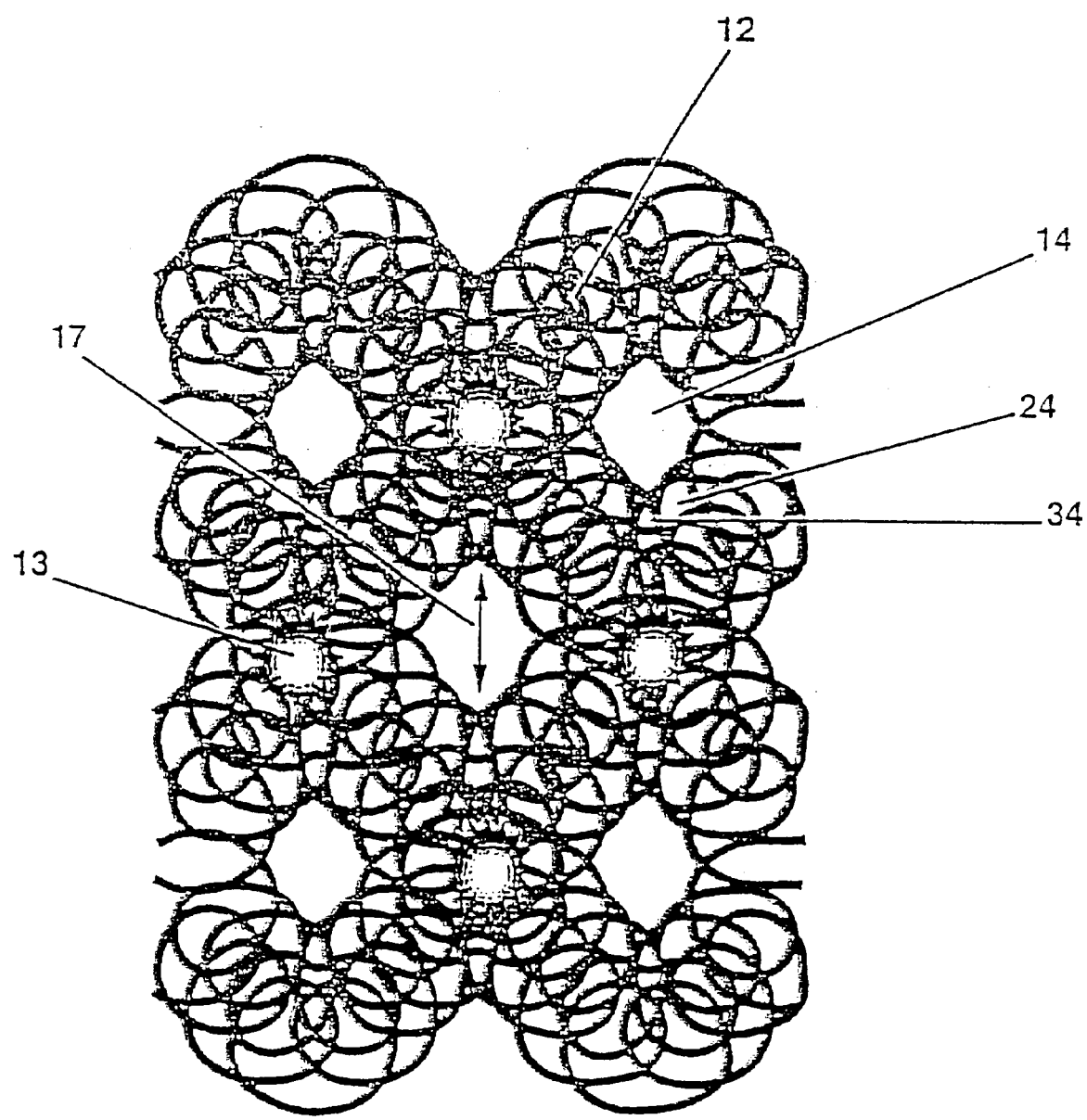
FIG. 2 is a diagrammatic plan view of a portion of the embroidered surface of a medical article according to the invention.

FIG. 2 shows a diagrammatic plan view of a portion of the embroidered surface 12 of a medical article 1 according to the invention. The structures designated with reference number 14 are openings which are provided in the embroidered pattern and which are substantially diamond-shaped here. In other configurations, these shapes can also be rectangular, round, elliptic or have another shape.

To positively stimulate angiogenesis, it is particularly advantageous that the openings at the center of the compress 1 have the greatest aperture area and form corresponding cavities. In the illustrative embodiment according to FIG. 2, a gradient is provided with which the diameters 17 of the openings provided decrease from the center to the edges.

The openings 14 are arranged in a regular pattern in the illustrative embodiment shown. The embroidery technology also permits an irregular arrangement of the openings 14 according to further objectives, in particular with a variation in size.

The fabric 11 mentioned with reference to FIG. 1 and lying behind the embroidered surface 12 acts as a spacer and distributes the weight upon loading in order to prevent decubitus ulcers. The predetermined hole cross sections 17 have a size forming a cavity suitable for a blood coagulum. They are therefore a support for the tissue-regenerating element.

Figure 3:
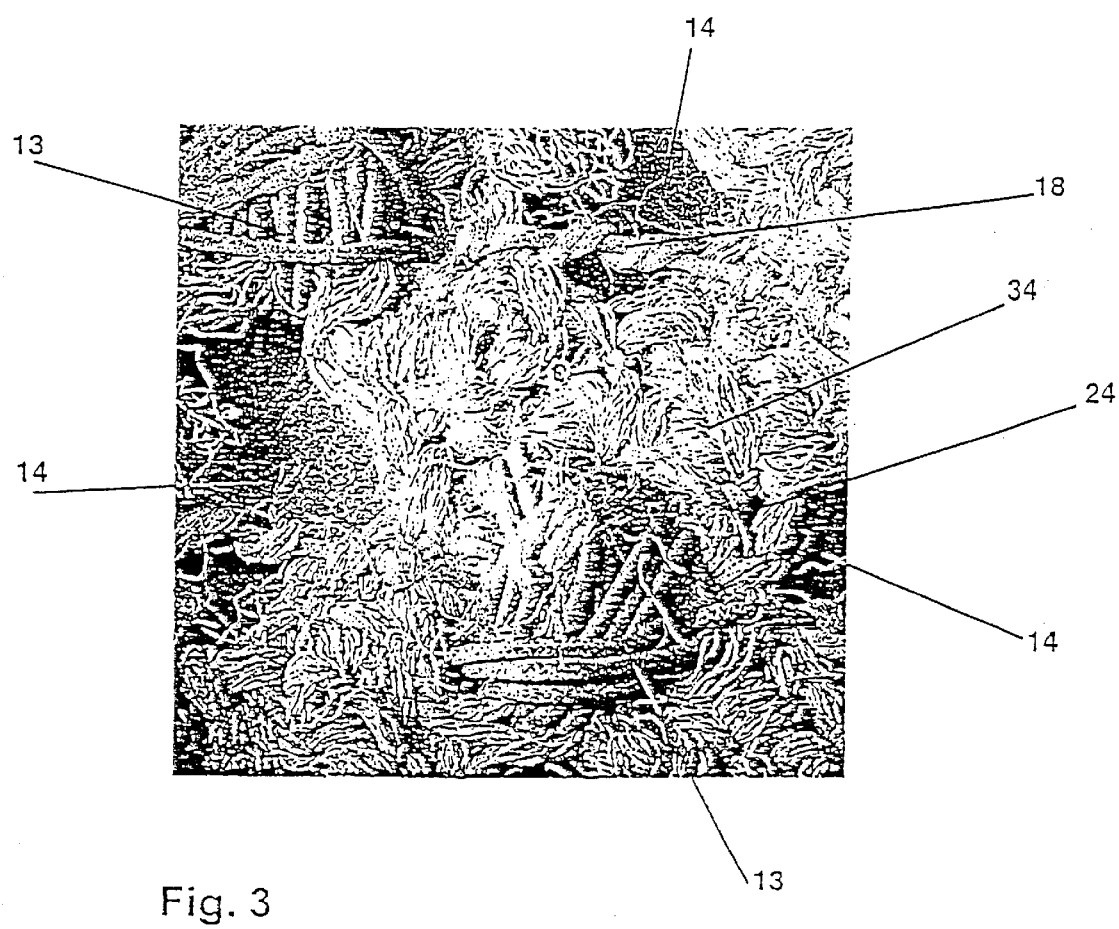
FIG. 3 is an enlarged sectional view of the area of a pore according to FIG. 2.

The embroidered surface, of which FIG. 3 shows a section of the area of a pore 14 according to FIG. 2, has mesoscopic openings 24 in addition to the apertures or pores 14.

The macroscopic apertures or pores 14 are produced by a plurality of links and have a size of the order of 1 to 2 millimeters edge length. They serve for ingrowth of tissue plugs and as a reservoir for the blood coagulum from the freshly bleeding wound.

The mesoscopic openings 24 permit ingrowth of individual blood vessel stems and have a size of approximately 100 to 500 micrometers. They are produced by interfacing of two yarn elements.

Also shown here in diagrammatic representation are microscopic openings 34 with a diameter in the range of 5 to 50 micrometers which permit the ingrowth of cells and cell aggregates with capillaries if necessary. These openings 34 are between different filaments.

On a still smaller scale, small cavities in the range of 0.5 to 5 micrometers are present between individual filaments, and only extracellular matrix, for example collagen material, can be deposited in these.

The openings 14, 24 and 34 form groups of hole patterns. The openings 14, the openings 24 and the openings 34 are greater or smaller in relation to another group of openings by a factor of approximately at least 5. Within each group the openings can to a certain extent be the same size or can be of different sizes. The distribution can be regular or also random in the sense that a device for embroidering a textile material controls the random distribution of the openings on the whole surface of the textile material with the aid of a random number generator.

Reference number 13 denotes an embroidery point which, in the illustrative embodiment shown, lies between two edges of the diamond-shaped openings 14. This embroidery point 13 is three-dimensional relative to the drawing plane and thus the plane of the embroidered layer 12 and has in particular a section protruding by 3 to 5 mm. In the illustrative embodiment shown, this is almost semispherical, but can also have other three-dimensional structures.

For example, this embroidery point can also be three-dimensional on the side pointing toward the knitted spacer, in particular in order to form an abutment.

In contrast to known knits, the regular arrangement of the embroidery shown in the figures is not system-related and instead can be changed as desired in accordance with the use on the basis of the embroidery technique. Thus, sequences of large and small apertures 14 are possible. As is shown in FIG. 2, these can have a gradient. The sequence of embroidery points 13 and openings 14 is purely functional and not dictated by the manufacturing technology of the textile fabric.

It is also possible that the apertures or pores 14 are spanned by a continuous thread 18 according to FIG. 3, which for example runs from knot to knot in the embroidery of knots 13.

The interplay of the different hole sizes of the openings 14, 24, 34 favorably influences the ingrowth of blood vessels, so-called angiogenesis. Main growths have a size of 0.5 to 1 mm here. By means of the embroidery points it is possible to create a mechanical stimulation in the wound bed, which affords an advantageous design of the embroidered compress material.

Monofilaments, multifilaments or mixtures of these can be used in the embroidery process. The strength of the embroidery can be determined through the choice of yarn and the specified pattern. An advantage over a knit is that the thread cannot move in the interfacings, that is to say the mechanical properties of the embroidery are defined by the arrangements of the interfacings and are hardly affected by the incorporation of exudate or extracellular matrix into the thread, which leads to the interfacings sticking together. In knits, by contrast, the mechanical properties are mainly defined by the movability of the thread through the open interfacing. Thus, an adhesive exudate leads to an increase in the rigidity of the textile in some circumstances far more than an order of size. This is a considerable disadvantage for the medical product since the mechanical properties which are crucial for its medical functionality can no longer be controlled. Stiffening can cause local loading conditions which can lead to local tissue necrosis.

In addition to the use of the embroidered element on a textile base such as a compress, other possible uses can also be envisaged. This can include the use of the embroidered surface material on a metallic or ceramic base or other wound-treating elements. The embroidery technique makes it possible to produce suitable surface elements for each individual case.

Having described presently preferred embodiments of the invention, it is to be understood that it may be otherwise embodied within the scope of the appended claims.

We claim:

1. A medical product with a textile component which forms a surface, said surface made from an embroidery, wherein the surface has a multiplicity of openings, there being at least two patterns of holes with groups of openings, each said hole pattern having a surface, the diameter of one opening of one hole pattern deviating from the diameter of an opening of another hole pattern in each case by about at least a factor of 5 from one another, and wherein a multiplicity of compact, rigid embroidered stimulation points is provided between the openings of the surface of each hole pattern, each said compact, rigid embroidered stimulation point having a surface, said stimulation point surface protruding from the textile component by several millimeters as a flat to semi-spherical protruberance, and further wherein the stimulation points serve as an angiopolar layer that inhibits tissue ingrowth thereon.

2. The medical product according to claim 1, wherein the embroidery comprises a structure selected from the group consisting of monofilaments, multifilaments, mixtures of monofilaments and multifilaments, and staple fiber yarns.

3. The medical product according to claim 1, wherein the hole pattern with the largest diameter of its openings and the hole pattern with the second largest diameter of its openings are arranged regularly.

4. The medical product according to claim 1, wherein the hole pattern with the largest diameters has the largest opening surface area in the middle of the product and decreases in a gradient toward the edges of the product.

5. The medical product according to claim 4, wherein the surface of the compact, rigid embroidered stimulation points correspond to the surface of the hole pattern with the largest diameters.

6. The medical product according to claim 4, wherein each compact, rigid embroidered stimulation point has a height of between about 3 to 5 millimeters.

7. The medical product according to claim 4, having two sides, wherein the compact, rigid embroidered stimulation points protrude from the embroidery plane of the textile product on both sides of the textile product.

8. The medical product according to claim 1, wherein the product comprises a product selected from the group consisting of a compress, a hernia mesh, an abdominal wall replacement, an artificial ligament and an augmentation textile for applications in the dental sector.

9. The medical product according to claim 1, wherein the textile component comprises an embroidery material selected from the group consisting of natural, synthetic, inorganic and mineral raw materials.

10. The medical product according to claim 1, wherein said textile component forms a first layer, said medical product further comprising a second layer which is a knitted spacer layer and a third layer which is a woven base layer.

11. The medical product according to claim 10, wherein the second layer is capable of taking up exudates and absorbing shear forces and the third layer has an antibacterial action.

\* \* \* \* \*